US00PP16590P2

(12) United States Plant Patent
Zaiger et al.

(10) Patent No.: US PP16,590 P2
(45) Date of Patent: May 30, 2006

(54) INTERSPECIFIC TREE NAMED 'FLAVOR FINALE'

(50) Latin Name: [***Prunus salicina*×(*Prunus salicina*× *Prunus armeniaca)***]
Varietal Denomination: Flavor Finale

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 142 days.

(21) Appl. No.: 10/994,622

(22) Filed: Nov. 23, 2004

(51) Int. Cl.
*A01H 5/00* (2006.01)

(52) U.S. Cl. ..... Plt./180
(58) Field of Classification Search ..... Plt./180
See application file for complete search history.

*Primary Examiner*—Anne Marie Grunberg

(57) ABSTRACT

A new and distinct variety of interspecific tree [*Prunus salicina*×(*Prunus salicina*×*Prunus armeniaca*)]. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Heavy and regular fruit production.
2. Producing fruit ripening in the late maturity season.
3. Fruit with firm flesh, good handling and storage quality.
4. The tree having vigorous, upright growth.
5. Fruit having firm, reddish yellow flesh with very good flavor and eating quality.
6. Fruit with high soluble solids (Brix) averaging 18.2°.

1 Drawing Sheet

Latin name of the Genus and Species of the Plant Claimed: [*Prunus salicina*×(*Prunus salicina*×*Prunus armeniaca*)].

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plum trees, which are known to us, and mentioned herein, are 'Queen Ann' Plum (non-patented), 'Casselman' Plum (non-patented), 'King David' Plum (non-patented), and 'Red Beaut' Plum (U.S. Plant Pat. No. 2,539).

STATEMENT REGARDING FEDERALLY SPONSORED RESEARCH AND DEVELOPMENT

Not applicable.

ORIGIN OF THE VARIETY

The new and distinct variety of interspecific tree [*Prunus salicina*×(*Prunus salicina*×*Prunus armeniaca*)] was originated by us in our experimental orchard, located near Modesto, Calif., as a first generation cross between 2 proprietary parents with field identification numbers '57RC99' and '4G1180'. The maternal parent (57RC99) originated from crosses between the following plums, 'King David' Plum (non-patented), 'Queen Ann' Plum (non-patented) and 'Casselman' Plum (non-patented). The paternal parent being the plumcot '4G1180' originated as a selected seedling from open pollinated 'Red Beaut' Plum (U.S. Plant Pat. No. 2,539) seed. A large number of seedlings from this first generation cross were budded to older trees of 'Nemaguard' Rootstock (non-patented), to accelerate rapid fruit production for evaluation. Under close and careful observation, one such seedling exhibited desirable tree growth and fruit characteristics and was selected in 1996 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of interspecific tree (Plum×Plumcot) is of large size, vigorous, upright growth and a productive and regular bearer of medium size, clingstone fruit with reddish yellow flesh, very good flavor and eating quality. The fruit is further characterized by having an attractive reddish maroon skin color, being relatively uniform in size throughout the tree, holding firm on the tree for approximately 3 weeks after maturity (shipping ripe) and having good handling and shipping quality. In comparison to the grandparent 'Casselman' Plum (non-patented), the variety to which the instant cultivar is most similar to, the fruit of the new variety is darker in color, more uniform in size and maturity, has higher soluble solids (Brix), heavier production of fruit and is approximately 10 days later in maturity. The winter chilling requirement being approximately the same for both varieties.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 8 year old specimens grown near Modesto, Calif., with color in accordance with Munsell Book of Color.

Tree:

*Size.*—Large. Usually pruned to 3 to 3.5 meters in height for economical harvesting of fruit.

*Vigor.*—Vigorous, growth of 1.5 to 2 meters in height the first growing season. Varies with soil type, fertility, climatic conditions and cultural practices.

*Form.*—Upright, usually pruned to vase shape.

*Branching habit.*—Upright. Crotch angle approximately 25° increases with heavy crop load.

*Productivity.*—Heavy, thinning and spacing of fruit necessary for desired market size fruit.

*Bearer.*—Regular, adequate fruit set 6 consecutive years, no alternate bearing observed.

*Fertility.*—Self sterile, pollenizer required.

*Density.*—Medium dense, pruned to vase shape to increase sunlight and air movement to center of tree to enhance fruit color and health of fruit spurs.

*Hardiness.*—Hardy in all stone fruit growing areas of California. Tree grown in USDA Hardiness Zone 9. Winter chilling requirement approximately 800 hours at or below 45° F.

Trunk:

*Size.*—Medium. Average circumference 48.2 cm at 17.7 cm above ground on an 8 year old tree.

*Texture.*—Medium shaggy, roughness increases with age.

*Color.*—Varies from 5YR 2/2 to 7.5YR 5/2.

Branches:

*Size.*—Medium. Average circumference 17.2 cm at 0.8 meters above ground.

*Surface texture.*—New growth smooth. Mature growth medium rough, roughness increases with age of branch.

*Lenticels.*—Large. Average number 21 in a 25.8 square cm surface. Average length 4.1 mm. Average width 1.3 mm. Color varies from 2.5YR 5/8 to 5YR 5/1.

*Color.*—New growth varies from 5GY 5/8 to 7.5YR 3/6, varies with exposure to direct sunlight. Old growth varies from 5YR 2/4 to 7.5YR 2/4, varies with age of growth.

Leaves:

*Size.*—Medium. Average length 78.7 mm. Average width 43.0 mm.

*Form.*—Obovate.

*Apex.*—Acuminate.

*Base.*—Cunate.

*Margin.*—Doubly serrate.

*Thickness.*—Medium.

*Surface texture.*—Upper surface relatively smooth, slightly indented over midrib and leaf veins, glabrous. Lower surface relatively smooth, small ridges created by midrib and pinnate venation, glabrous.

*Petiole.*—Average length 15.0 mm. Average width 1.4 mm. Longitudinally grooved. Glabrous. Color varies from 2.5GY 7/6 to 5GY 7/6.

*Glands.*—Type— globose. Small to medium. Average length 0.9 mm. Average diameter 0.5 mm. Average number 2, varies from 2 to 4. Primarily located on upper portion of petiole and base of leaf blade. Color varies from 5GY 7/6 to 2.5YR 5/6.

*Color.*—Upper surface varies from 5GY 3/4 to 5GY 3/6. Lower surface varies from 5GY 5/4 to 5GY 4/4. Midvein color varies from 2.5GY 9/6 to 5GY 8/4.

Flower buds:

*Size.*—Small. Average length 10.4 mm. Average diameter 5.5 mm.

*Hardiness.*—Hardy in all stone fruit growing areas of California.

*Form.*—Conical, becomes slightly elongated just before opening.

*Pedicel.*—Surface — glabrous. Average length 9.1 mm. Average width 0.6 mm. Color varies from 2.5GY 6/8 to 5GY 7/6.

*Color.*—N 9.5/.

*Number of buds per spur.*—Average 9, varies from 2 to 18.

Flowers:

*Size.*—Medium. Average height 9.7 mm. Average diameter 16.6 mm.

*Petals.*—Number — 5, alternately arranged to sepals. Form — obovate, narrows at point of attachment. Size — small to medium. Average length 9.4 mm. Average width 7.3 mm. Margin — sinuate. Both surfaces glabrous. Color — N 9.5/.

*Sepals.*—Number — 5, alternately arranged to petals. Shape — triangular, apex rounded. Margin — entire. Size — small. Average length 2.9 mm. Average width 2.0 mm. Both surfaces glabrous. Color — upper surface varies from 2.5GY 5/8 to 5GY 5/8. Lower surface varies from 2.5GY 5/6 to 5GY 5/6.

*Stamens.*—Average number 27. Average filament length 6.5 mm. Filament color N 9.5/. Anther color varies from 2.5Y 8/12 to 5Y 8/10.

*Pollen.*—Self sterile, pollenizer required. Color varies from 2.5Y 7/10 to 5Y 7/10.

*Pistil.*—Usually 1, varies from 1 to 2. Average length 8.8 mm. Position of stigma approximately same height as anthers. Surface glabrous. Color varies from 2.5GY 8/6 to 5GY 8/6.

*Fragrance.*—Moderate aroma.

*Blooming period.*—Date of First Bloom Feb. 26, 2004. Date of Petal Fall Mar. 6, 2004, varies slightly with climatic conditions.

*Color.*—N 9.5/.

*Number flowers per flower bud.*—Average 2 , varies from 1 to 3.

*Pedicel.*—Average length 12.1 mm. Average width 0.6 mm. Color varies from 2.5GY 6/8 to 5GY 7/8.

Fruit:

*Maturity when described.*—Firm ripe.

*Date of first picking.*—Aug. 10, 2004.

*Date of last picking.*—Aug. 17, 2004, varies slightly with climatic conditions.

*Size.*—Medium. Average diameter axially 55.0 mm. Average transversely in suture plane 59.6 mm. Average weight 119.3 grams. Average weight varies slightly with fertility of the soil, amount of thinning and climatic conditions.

*Form.*—Cordate.

*Suture.*—Shallow, extends from base to apex.

*Ventral surface.*—Nearly smooth, slightly lipped.

*Apex.*—Varies from slight projection to slightly pointed.

*Base.*—Varies from flat to slightly retuse.

*Cavity.*—Rounded to elongated in suture plane. Average depth 4.9 mm. Average breadth 8.4 mm.

Stem:

*Size.*—Small to medium. Average length 12.6 mm. Average diameter 1.7 mm.

*Color.*—Varies from 2.5GY 7/8 to 2.5GY 6/6.

Flesh:

*Ripens.*—Evenly.

*Texture.*—Firm, meaty.

*Fibers.*—Small, tender.

*Firmness.*—Firm, slightly firmer than 'Casselman' Plum (non-patented).

*Aroma.*—Slight.

*Amydgalin.*—Undetected.

*Eating quality.*—Very good.

*Flavor.*—Very good, good balance between acid and sugar.

*Juice.*—Moderate, enhances flavor.

*Brix.*—Average 18.2°, varies slightly with amount of fruit per tree and climatic conditions.

*Color.*—Varies from 10YR 8/6 to 10YR 7/8 near center to 5R 4/10 near skin surface. Pit cavity varies from 7.5YR 5/6 to 7.5YR 5/8.

Skin:

*Thickness.*—Medium.

*Surface.*—Smooth.

*Bloom.*—Moderate amount, complete coverage.

*Tendency to crack.*—None.

*Color.*—Ground color varies from 2.5Y 8.5/6 to 5Y 8/4. Overspread with 2.5R 3/8 to 5R 2/6. Very small, randomly spaced, areas of ground color exposed to skin surface giving a speckled pattern.

*Tenacity.*—Tenacious to flesh.

*Astringency.*—None.

Stone:

*Type.*—Clingstone.

*Size.*—Medium. Average length 27.0 mm. Average width 16.8 mm. Average thickness 9.9 mm.

*Form.*—Obovoid.

*Base.*—Pointed.

*Apex.*—Pointed. Average length 0.9 mm.

*Surface.*—Lightly pitted throughout, one small groove on each side of suture.

*Sides.*—Unequal, one side extending further from the suture plane.

*Ridges.*—One small, narrow ridge along groove near suture.

*Tendency to split.*—None.

*Color.*—Varies from 7.5YR 5/6 to 7.5YR 4/6 when dry.

Kernal:

*Form.*—Ovate.

*Taste.*—Bitter.

*Viability.*—Viable, complete embryo.

*Size.*—Small. Average length 13.8 mm. Average width 9.1 mm. Average thickness 5.6 mm.

*Skin.*—Color varies from 7.5YR 5/8 to 10YR 7/6.

Use: Dessert.

*Market.*—Local and long distance.

Keeping quality: Good, stored 2 weeks at 38° to 42° F., fruit was still firm without internal breakdown or appreciable loss of flavor.

Shipping quality: Good, minimal skin scarring or bruising of flesh during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

What is claimed is:

1. A new and distinct variety of interspecific tree, (Plum× Plumcot), substantially as illustrated and described, characterized by its large size, vigorous, upright growth and being a regular and productive bearer of medium size, firm, reddish yellow flesh with very good flavor and eating quality; the fruit is further characterized by being relatively uniform in size throughout the tree and holding firm on the tree approximately 3 weeks after maturity (shipping ripe).

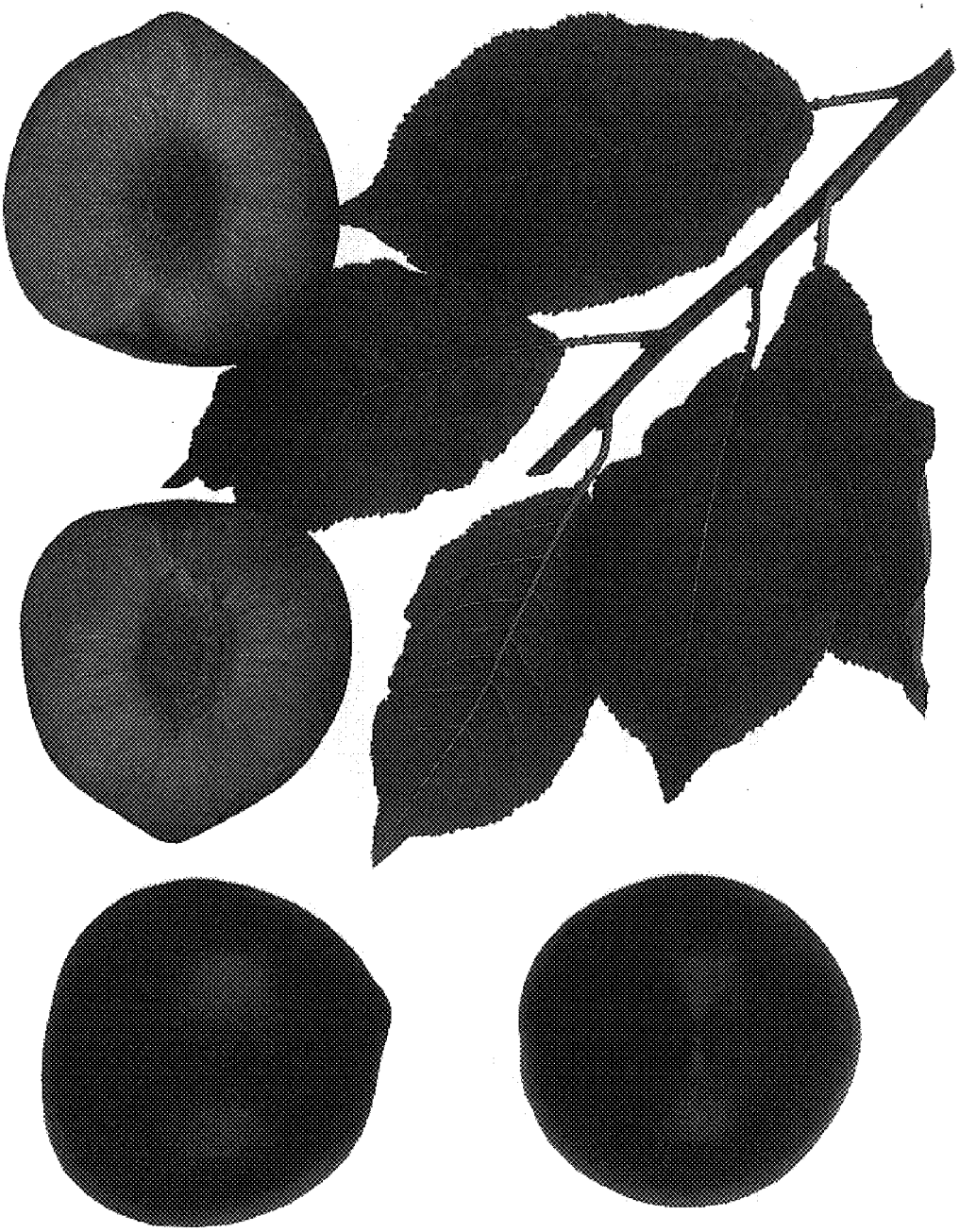

* * * * *